United States Patent [19]
Ooka et al.

[11] Patent Number: 5,730,977
[45] Date of Patent: Mar. 24, 1998

[54] ANTI-VEGF HUMAN MONOCLONAL ANTIBODY

[75] Inventors: Hisayoshi Ooka; Shiro Takagi; Izumi Mita; Noboru Satozawa; Ayako Watanabe; Tomoko Yokomatsu, all of Chiba-ken, Japan

[73] Assignee: Mitsui Toatsu Chemicals, Inc., Tokyo, Japan

[21] Appl. No.: 698,041

[22] Filed: Aug. 15, 1996

[30] Foreign Application Priority Data

Aug. 21, 1995 [JP] Japan .................................. 7-211454
Mar. 22, 1996 [JP] Japan .................................. 8-066601

[51] Int. Cl.$^6$ .......................... A61K 39/395; C12N 5/00; C12P 21/08
[52] U.S. Cl. .................. 424/141.1; 435/335; 530/388.1; 424/130.1; 424/138.1; 424/142.1
[58] Field of Search .............................. 424/130.1, 138.1, 424/141.1, 142.1; 435/240.27; 530/388.1

[56] References Cited

FOREIGN PATENT DOCUMENTS 0368662  5/1990  European Pat. Off. .
WO 94 10202  5/1994  WIPO .

OTHER PUBLICATIONS

Joan W. Miller et al, "Vascular Endothelial Growth Factor/ Vascular Permeability Factor is Temporally and Spatially Correlated with Ocular Angiogenesis in a Primate Model", *American Journal of Pathology*, (1994) 145:574–584, No. 3.
K. Jin Kim, "The Vascular Endothelial Growth Factor Proteins: Identification of Biologically Relevant Regions by Neutralizing Monoclonal Antibodies", *Growth Factors* (1992) 7:53–64.
Shinichi Kondo et al., "Significance of Vascular Endothelial Growth Factor/Vascular Permeability Factor for Solid Tumor Growth, and its Inhibition by the Antibody" *Biochemical and Biophysical Research Communications*, (1993) 194:1234–1241, No. 3.

K. Jin Kim, "Inhibition of Vascular Endothelial Growth Factor-Induced Angiogenesis Suppresses Tumour Growth in vivo" *Letters to Nature*, (1993) 362:841–844.

Klaus Bendtzen et al, "Autoantibodies to Cytokines— Friends or Foes? *Immunology Today*, (1990) 11:167–169, No. 5.

Petra Boyle et al., "A Novel Monoclonal Human IgM Autoantibody which Binds Recombinant Human and Mouse Tumor Necrosis Factor–α", *Cellular Immunology*, (1993) 152:556–568.

Carson & Frieman K (Advances in Immunology, 1986, 38:275–311).

Fan et al (Trends in Pharmacology Sci, Feb., 1995, 16:57–66).

Rockwell et al (Mol Cell Dif, Mar. 1995, 3:91–109).

*Primary Examiner*—Lila Feisee
*Assistant Examiner*—Susan Ungar
*Attorney, Agent, or Firm*—Burns, Doane, Swecker & Mathis

[57] ABSTRACT

The present invention provides an anti-VEGF human monoclonal antibody capable of binding to human VEGF to neutralize its activity, a cell strain producing said human monoclonal antibody, and a vascularization inhibitor containing said human monoclonal antibody. Hybridoma strains VA01 and BL2 producing the anti-VEGF human monoclonal antibody can also be provided according to the present invention by transformation with Epstein-Barr Virus (EBV) of human lymphocyte producing anti-human VEGF antibody and then fusing the transformant cells with human myeloma cells. The monoclonal antibody of the present invention can serve as a vascularization inhibitor which is useful for human because it is derived from human and capable of binding specifically to VEGF participating in vascularization, to inhibit the migration or proliferation of vascular endothelial cells.

8 Claims, 4 Drawing Sheets

Binding Ability of Anti-VEGF Human Monoclonal Antibodies to Human VEGF Antigen in Liquid Phase Inhibition Test of Anti-VEGF Human Monoclonal Antibody of Migration of Vascular Endothelial Cells Inhibition Test of Anti-VEGF Human Monoclonal Antibody of Proliferation of Vascular Endothelial Cells

ANTI-VEGF HUMAN MONOCLONAL ANTIBODY

FIELD OF THE INVENTION

The present invention relates to human monoclonal antibodies. More specifically, the present invention relates to human monoclonal antibodies having the ability to neutralize the vascularization activity of human vascular endothelial cell growth factor (referred to hereinafter as "human VEGF") by binding to human VEGF as well as a novel vascularization inhibitor containing said human monoclonal antibodies.

BACKGROUND OF THE INVENTION

Vascular endothelial cell growth factor (VEGF) is a growth factor acting specifically on vascular endothelial cells to promote their vascularization. It is known that vascularization plays an important role in development, wound treatment, inflammation etc. and is further involved in pathological conditions such as diabetic retinopathy, tumor formation, etc. The vascularization consists of 4 steps (1) destruction and degradation of basement membrane by proteases, (2) migration of endothelial cells (3) proliferation of endothelial cells, and (4) differentiation of endothelial cells and formation of tubes and cavities. It is estimated that VEGF is involved in the step of migration of endothelial cells and the subsequent steps.

It is known that the growth of a solid tumor requires tumor vascularization for supplying oxygen and nutrients and the metastasis of tumor cells occurs through blood vessels resulting from the tumor vascularization. VEGF is believed to play a primary role in this vascularization for tumors. Therefore, it is expected that the growth and metastasis of tumor can be inhibited by a certain substance neutralizing the vascularization activity of VEGF.

In nearly half of diabetics there occurs an eye disease i.e. diabetic retinopathy as one of complications of diabetes. It is believed that the formation of microcapillaries is promoted in diabetic retinopathy by oxygen deficiency and these microcapillaries will sooner or later be ruptured to bleed to form scar tissue, leading to detached retinas. Hence, it is expected that inhibition of vascularization can prevent retinopathy from developing critically. Based on experiments using monkey, Miller et al. reported that VEGF is related very closely to the development of vegetative retinopathy (Miller et al.: Am. J. Pathol. 145, 574–584 (1994)). For this reason, a substance neutralizing the vascularization activity of VEGF is considered useful for preventing or treating diabetic retinopathy.

With the background as described above, mouse monoclonal antibodies or rabbit polyclonal antibodies against VEGF have been prepared as substances neutralizing the vascularization activity of VEGF.

For example, Kim et al. immunized a mouse with human VEGF as an antigen, then subjecting spleen cells obtained from the mouse to cell fusion with myeloma cells to prepare a hybridoma, and obtaining anti-VEGF mouse monoclonal antibodies from the hybridoma (Kim et al.: Growth Factors 7, 53–64 (1992)). Kondo et al. immunized a rabbit with human VEGF as an antigen to prepare anti-VEGF rabbit polyclonal antibodies from the serum (Kondo et al.: Biochem. Biophys. Res. Commun. 194, 1234 (1993)). Upon administration into a nude mouse having tumor cells transplanted in it, these antibodies are reported to inhibit the growth of the tumor cells (see, for example, Kim et al., Nature 362, 841 (1993); WO94/10202; and Japanese Patent Application LOP Publication No. 116,163/1994).

However, these reports contain a mere description of anti-VEGF monoclonal and polyclonal antibodies derived from animals excluding human, and there is no description therein of anti-VEGF monoclonal antibodies derived from human.

Such antibodies derived from different species of animals other than human, upon administration to human, are recognized as foreign substances. As a result, various antibody reactions occur and generate antibodies against said administered animal antibodies. Given the antibody reactions, the reactivity of the administered antibodies themselves is decreased while their half-life in human blood is significantly reduced. For example, if mouse monoclonal antibodies are administered to human, human anti-mouse antibody reaction (HAMA) will occur.

For reduction of HAMA, it is attempted to prepare chimera antibodies or humanized antibodies by recombination of the antigen binding site of a mouse monoclonal antibody and the constant region of a certain human antibody. However, HAMA cannot completely be prevented from occurring by this method, too, because the components derived from the mouse antibody are recognized as antigens in human bodies.

Under these circumstances, it is understood that complete anti-VEGF human monoclonal antibodies will be useful.

However, it is uncertain whether antibodies binding to human VEGF or antibodies capable of neutralizing the vascularization activity of human VEGF are present in healthy human bodies. Because human VEGF is one of the biological components in human, it is naturally not possible for those skilled in the art to anticipate the possibility of obtaining antibodies against it. In fact, anti-VEGF human monoclonal antibodies have never been obtained.

Nevertheless, Bendzten et al. have reported that a binding activity of autoantibodies against some cytokines are present in serum (e.g. Bendzten et al.: Immunol Today 11, 167–169 (1990)). However, the report made by Bendzten et al. is concerned with cytokines acting on only the immune system, where no antibody has been isolated. Further, they have suggested that these autoantibodies may participate in the regulation of the life of cytokines, e.g. contribution to cytokine stabilization in blood by binding, delay in excretion into urine, etc. That is, the autoantibodies reported by Bendzten et al. are those against cytokines acting on the immune system, and there is no report on autoantibodies against cytokines (e.g. VEGF) not participating in the immune system.

In an example of the preparation of human monoclonal antibodies against human biological components, Boyle et al. have obtained human monoclonal antibodies against human tumor necrosis factor (TNF) (Boyle et al.: Cell Immunol 152, 556–568 (1993)). The antibodies thus obtained bind to TNF located on a cell surface or bound to a solid phase, but they do not bind to TNF keeping its stereo structure in a liquid phase, nor can they neutralize TNF activity.

That is, their monoclonal antibodies are those not binding to a biological component with its stereo structure kept normal in vivo.

From the foregoing, the presence of autoantibodies against cytokine in serum from healthy human bodies was known, but the presence of autoantibodies capable of serving as treatment agents for inhibiting cytokine action by binding specifically to cytokine having a normal stereo structure in vivo was not known.

As described above, it was absolutely uncertain whether anti-VEGF human monoclonal antibodies can be obtained or not. As a matter of course, there were not known any antibody capable of neutralizing the vascularization activity of human vascular endothelial cells induced by human VEGF.

SUMMARY OF THE INVENTION

The object of the present invention is to provide anti-VEGF human monoclonal antibodies. More specifically, the object of the present invention is to provide human monoclonal antibodies which can bind to human VEGF to neutralize the vascularization activity of human VEGF. Another object of the present invention is to provide a novel vascularization inhibitor expected to treat and prevent cancer or diabetic retinopathy.

As a result of their eager study, the present inventors found that human monoclonal antibodies binding to human VEGF can be obtained from human lymphocyte, and they further found that their antibodies can inhibit some vascularization activities induced by human VEGF, i.e. the migration activity of vascular endothelial cells and the proliferation activity of vascular endothelial cells, so that they completed the present invention.

According to the present invention, there are provided anti-VEGF human monoclonal antibodies binding to human VEGF and a novel vascularization inhibitor containing said human monoclonal antibodies. These monoclonal antibodies can be expected to prevent and treat diseases resulting from vascularization by virtue of their ability to inhibit the vascularization of human VEGF believed to be involved closely in tumor vascularization and diabetic retinopathy. There are further disclosed human monoclonal antibodies free of antigenicity upon administration to human, in contrast to conventional anti-VEGF mouse monoclonal antibodies and anti-VEGF rabbit polyclonal antibodies reported so far as specific inhibitors of VEGF. Owing to these characteristics, a drug containing the anti-VEGF human monoclonal antibodies provided by the present invention is expected to serve as a vascularization inhibitor useful in human.

DETAILED DESCRIPTION OF THE INVENTION

Figure 1:
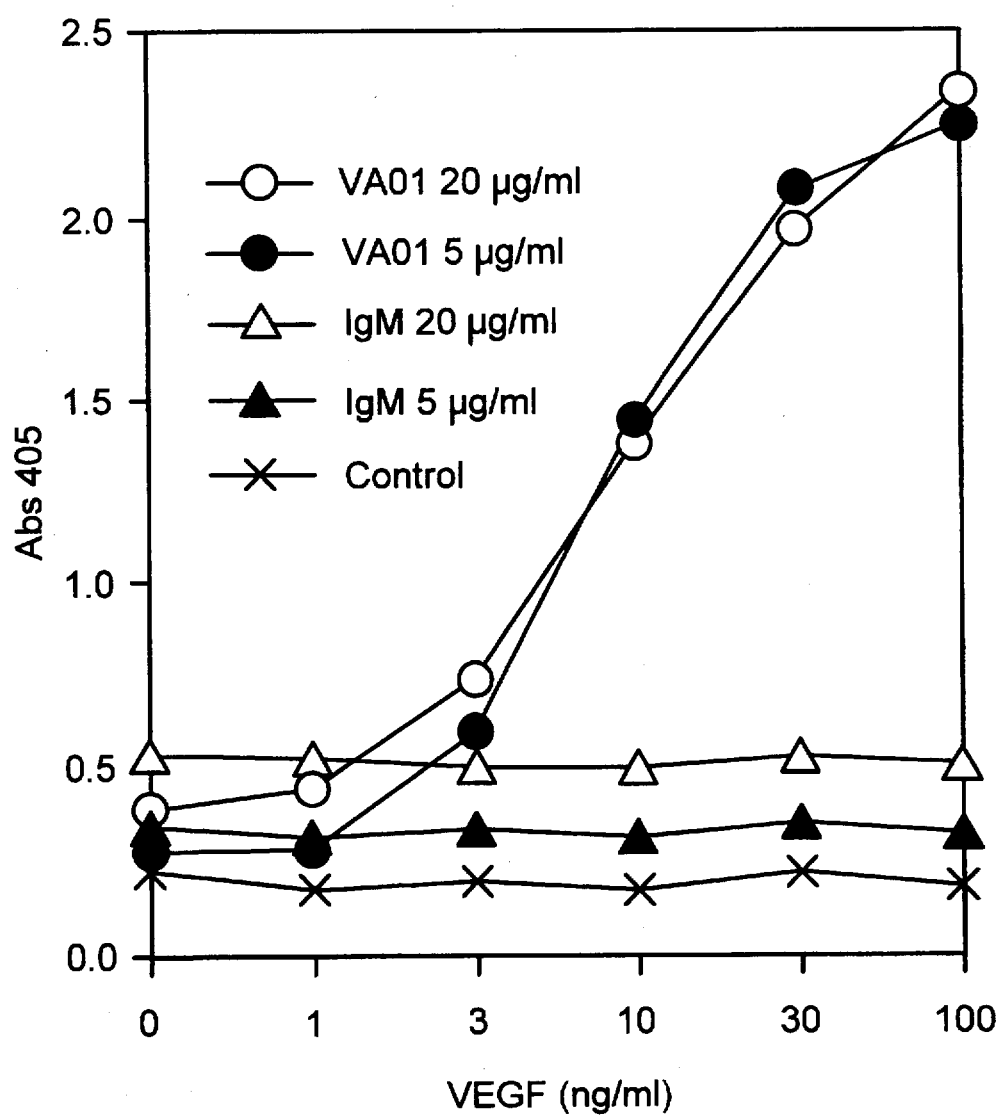
FIG. 1 shows the binding of anti-VEGF human monoclonal antibody to human VEGF antigen in a liquid phase, where VA01 is anti-VEGF human monoclonal antibody purified from hybridoma strain VA01, and IgM is human IgM antibody (Rockland). The concentration of each antibody is 20 and 5 µg/ml.

The human monoclonal antibodies of the present invention are those derived from human lymphocyte. The globulin type of the human monoclonal antibodies of the present invention is not particularly limited insofar as they have the ability to bind to human VEGF, and examples are IgG, IgM, IgA, IgE, IgD etc. The human monoclonal antibodies of the present invention are not limited insofar as they possess the ability to bind to human VEGF, and they include not only those obtained from a cell line producing such human monoclonal antibodies, but also fragments thereof prepared by enzymatic digestion, gene recombination, etc., and fusion proteins thereof with another protein or factor, etc. Such antibodies may be modified by gene recombination insofar as their ability to bind to VEGF is not deteriorated. In particular, the anti-VEGF human monoclonal antibodies of the present invention neutralize the vascularization activity of human VEGF. This vascularization is a phenomenon consisting of the steps (1) destruction and degradation of basement membrane by proteases (i.e. decomposition of intercellular matrix protein), (2) migration of endothelial cells, (3) proliferation of endothelial cells, and (4) differentiation of endothelial cells and formation of tubes and cavities. Hence, it is considered that the vascularization can be inhibited by inhibiting at least one of these steps. The inhibition of vascularization by antibody can be checked by examination of the effect of the antibody on the reaction in each step. The anti-VEGF monoclonal antibodies of the present invention can inhibit the vascularization by inhibiting the migration of vascular endothelial cells, or the proliferation of vascular endothelial cells, as vascularization activities induced by human VEGF.

The cell strain producing the anti-VEGF human monoclonal antibodies of the present invention is not particularly limited insofar as it can produce anti-VEGF human monoclonal antibodies. The cell strain can be obtained by transformation with Epstein-Barr Virus (EBV) of human lymphocyte producing anti-human VEGF antibodies. The cells can be obtained as hybridoma prepared by cell fusion between the resulting transformant and human myeloma cells. The cells can also be obtained as hybridoma by cell fusion between human lymphocyte producing anti-human VEGF antibodies and human myeloma cells. Alternatively, an antibody gene is removed from human lymphocyte producing anti-human VEGF antibodies and then integrated into a suitable vector to give producer cells. Examples of such cell strains producing anti-VEGF human monoclonal antibodies include hybridoma strains VA01 (FERM BP-5607) and BL2 (FERM BP-5424). Human lymphocyte producing anti-human VEGF antibodies, from which a cell strain producing the human monoclonal antibodies of the present invention is derived, can be obtained from human peripheral blood, lymph node etc. Any lymphocyte being present in human bodies and capable of producing antibodies having the ability to bind to human VEGF can be used in the present invention. The immunization of mouse, rabbit etc. with VEGF, usually conducted for acquiring monoclonal or polyclonal antibodies, is not required.

The preparation of the human monoclonal antibodies of the present invention from the cell strain producing anti-VEGF human monoclonal antibodies can be carried out by any of the culture and purification methods known in the art, and these methods are not particularly limited insofar as the growth of cells and the production of anti-VEGF human monoclonal antibodies are not inhibited.

The vascularization inhibitor of the present invention contains the anti-VEGF human monoclonal antibodies described above and is expected to be useful in preventing or treating diseases such as cancer, diabetic retinopathy etc. in which vascularization is involved.

EXAMPLES

The present invention is illustrated by reference to the following examples which are however not intended to limit the scope of the invention.

EXAMPLE 1

Preparation of Anti-VEGF Human Monoclonal Antibody (a) Transformation with EBV 20 ml peripheral blood was collected from a healthy person and a human mononuclear fraction was obtained by separating blood cells with a Ficoll separating solution (Dainippon Pharmaceutical Co., Ltd., Japan). It was washed twice with RPM-1640 medium (Nissui Seiyaku K. K., Japan) to prepare $3\times10^7$ human mononuclear cells. The human mononuclear cells were centrifuged at 1,600 r.p.m. for 6 minutes to give a pellet. The pellet was suspended again with 30 ml culture supernatant of B95-8 cells at 37° C. (i.e. a culture supernatant obtained by culturing B95-8 cells in RPMI-1640 medium containing 20% fetal calf serum (FCS)). This suspension was transferred to a $CO_2$ gas incubator at 37° C. and then infected with EBV for 90 minutes at the same temperature. This suspension was centrifuged at 1,600 r.p.m. for 6 minutes to give a pellet. This pellet was suspended in 60 ml RPMI-1640 medium containing 20% FCS and then pipetted into six 96-wells plates (Corning). The plates were transferred to a $CO_2$ gas incubator at 37° C. and incubated while half of the medium was exchanged with fresh one every 3 to 5 days.

(b) Confirmation of Antibody Production

Colony formation occurred in wells on the plates after 20 days of culture, and the culture supernatant in the wells was examined for antibody activity by dot immmunobinding assay (DIBA) with human VEGF as antigen, as follows. Recombinant human VEGF (PeproTech) as antigen was dissolved at a concentration of 50 µg/ml in water, then spotted in an amount of 0.2 µl per spot on a nitrocellulose membrane (a product of Toyo) equipped with a grid, and dried in air to immobilize the antigen on the membrane. The immobilized antigen was blocked with a blocking solution (Tris-HCl buffered saline (TBS) containing 10% FCS). 50 µl of the culture supernatant was put to each well on 96-wells U-bottomed plate, and the blocked, immobilized antigen was then added to it, and the plate was incubated at room temperature for 2 hours. Each well was washed with TBS, and 50 µl peroxidase-labeled anti-human immunoglobulin antibodies (produced by DAKO), previously diluted 500-fold with the blocking solution, was added to each well. The plate was incubated at room temperature for 2 hours. Each well was washed with TBS and stained with Konica Immustein (a product of Konica Corporation) and its coloration was checked with eyes. The same procedure was repeated 29 times for screening of 12,800 samples. As a result, anti-VEGF antibody activity was found in 2 wells.

(c) Cell Fusion

The cells found to have the antibody activity in (b) above were further cultured in 6-wells plate. The cells ($2 \times 10^6$ cells), and $1\times10^6$ SHM-D33 cells (obtained from ATCC) previously cultured in IMDM medium containing 20% FBS, were placed in a centrifuge tube and centrifuged at 1,600 r.p.m. for 6 minutes to give a pellet. This pellet was then washed twice with a cell fusion medium (0.25M mannitol, 0.1 mM calcium chloride, 0.1 mM magnesium chloride, 0.2 mM Tris-HCl buffer (pH 7.2)) to give a pellet again. The pellet was then suspended again in 0.4 ml cell fusion medium and subjected to electric cell fusion (fusion apparatus, Shimadzu SSH-1; fusion chamber, Shimadzu FTC-02). This fusion made use of alternating-current high-frequency electrical field (1 MHz, 40 V, 10 seconds) and direct-current pulse electrical field (2.3 kV/cm, 40 µs, 10 seconds). After fusion, the cells were suspended in IMDM medium containing HAT (Sanko Junyaku) and 1 µM uabain, 20% FCS, 5 µg/ml human transferrin, 8 µg/ml bovine insulin and 50 mM 2-mercaptoethanol and then put to each well in a 96-wells plate. The plate was transferred to a $CO_2$ gas incubator at 37° C. and incubated while half of the medium was exchanged with fresh one every 3 to 5 days. After 14 to 20 days of incubation, colony formation had occurred on wells, and the culture supernatant in the wells examined for antibody activity by the DIBA method described in (b) above. The cells found to have the antibody activity were cloned 3 times by limiting dilution to give hybridoma strains VA01 and BL2 producing anti-VEGF human monoclonal antibodies. The hybridoma strains VA01 and BL2 have been deposited under the Budapest Treaty as FERM BP-5607 and FERM BP-5424 respectively with the National Institute of Bioscience and Human-Technology, Agency of Industrial Science and Technology, Ministry of International Trade and Industry, of 1-3, Higashi 1 chome, Tsukuba-shi, Ibaraki-ken, 305, Japan; strain VA01 was deposited under Japanese Patent Law on Jul. 20, 1995, and assigned No. FERM P-15053, and transferred to deposit under the Budapest Treaty on Jul. 25, 1996, and assigned No. FERM BP-5607 in said depository; and strain BL2 was deposited under the Budapest Treat on Feb. 27, 1996, and assigned No. FERM BP-5424 in said depository.

d) Preparation of Antibodies

Hybridoma strains VA01 and BL2 were cultured in serum-free medium ASF-101 (a product of Ajinomoto Co., Ltd.) to give 350 ml culture supernatant. This culture supernatant was fractionated with 50% saturation with ammonium sulfate, and then the precipitates were dissolved again in phosphate buffered saline (PBS). The solution was filtered through 0.2 µm filter and purified through Superdex 200 column (produced by Pharmacia). The antibody fraction thus obtained was concentrated through an ultrafiltration membrane (30 k fractionation, Fuji Filter), then filtrated through a filter (0.2 µm) under sterile conditions, divided into aliquots and lyophilized –80° C. for storage before use.

EXAMPLE 2

Confirmation (1) of the Binding of Anti-VEGF Human Monoclonal Antibody to Human VEGF Antigan by Sandwich Elisa Method Anti-VEGF rabbit polyclonal antibody (PeproTech) was diluted to 4 µg/ml in 0.1M carbonate buffer (pH 9.6) and then put to a 96-wells plate (Greiner) in an amount of 50 µl per well. The plate was left at 4° C. overnight to have the antibody immobilized on it. This plate was washed with a washing solution (10 mM Tris-HCl buffer (pH 8.0) containing 0.02% sodium azide and 0.05% Tween 20) and blocked with a blocking solution (PBS containing 0.5% bovine serum albumin (BSA)). Separately, 20 and 5 µg/ml anti-VEGF human monoclonal antibody purified from hybridoma strain VA01 were mixed with 0 to 100 ng/ml human VEGF antigen (PeproTech) in another 96-wells U-bottomed plate, and this plate was incubated at room temperature for 2 hours. The reactant was transferred to the above antibody-immobilized plate after blocking and then incubated at room temperature for 2 hours. The plate was washed with the washing solution, and 100 µl alkaline phosphatase-labeled anti-human IgM antibody (BIO SOURCE) diluted 500-fold with the block solution was then put to each well, followed by incubation at room temperature for 2 hours. The plate was washed with the washing solution, and 50 µl substrate solution (9.6% diethanolamine buffer (pH 9.6) containing 0.6% p-nitrophenyl phosphoric acid and 0.5 mM magnesium chloride) was then put to each well, followed by incubation at room temperature for 30 minutes. The reaction was stopped by adding 50 µl of 3N sodium hydroxide to the reaction solution, and then the absorbance of each well at 405 nm was measured in Immuno Reader (produced by Nippon Intermed).

The results indicated that the antibody prepared from hybridoma strain VA01 reacts depending on the amount of human VEGF antigen added, as shown in FIG. 1. When the same reaction was carried out using another human IgM antibody (Rockland) of different specificity in place of the VEGF human monoclonal antibody or in the absence of the human monoclonal antibody (control), none of the reaction with human VEGF was observed. This indicated that the anti-VEGF human monoclonal antibody produced by hybridoma strain VA01 can recognize human VEGF in liquid phase to bind to it.

EXAMPLE 3
Confirmation (2) of the Binding of Anti-VEGF Human Monoclonal Antibody to Human VEGF Antigen by Sandwich Elisa Method According to Example 2, a plate having the antibody immobilized on it was prepared and blocked. Separately, 0.25 µg/ml anti-VEGF human monoclonal antibodies purified from hybridoma strains VA01 and BL2 were mixed with 0 to 100 ng/ml human VEGF antigen (PeproTech) in another 96-wells U-bottomed plate, and the mixture was incubated at room temperature for 2 hours. The reactant was transferred to the above antibody-immobilized plate after blocking and then incubated at room temperature for 2 hours. The plate was washed with the washing solution, and 100 µl anti-human IgM antibody (BIO SOURCE) labeled with alkaline phosphatase and diluted 500-fold with the blocking solution was then put to each well, followed by incubation at room temperature for 2 hours. The plate was washed with the washing solution, and 50 µl of a substrate solution (9.6% diethanolamine buffer (pH 9.6) containing 0.6% p-nitrophenyl phosphoric acid and 0.5 mM magnesium chloride) was then put to each well, followed by incubation at room temperature for 30 minutes. The reaction was stopped by adding 50 µl of 3N sodium hydroxide to the reaction solution, and the absorbance of each well at 405 nm was measured in Immuno Reader (Nippon Intermed).

Figure 2:
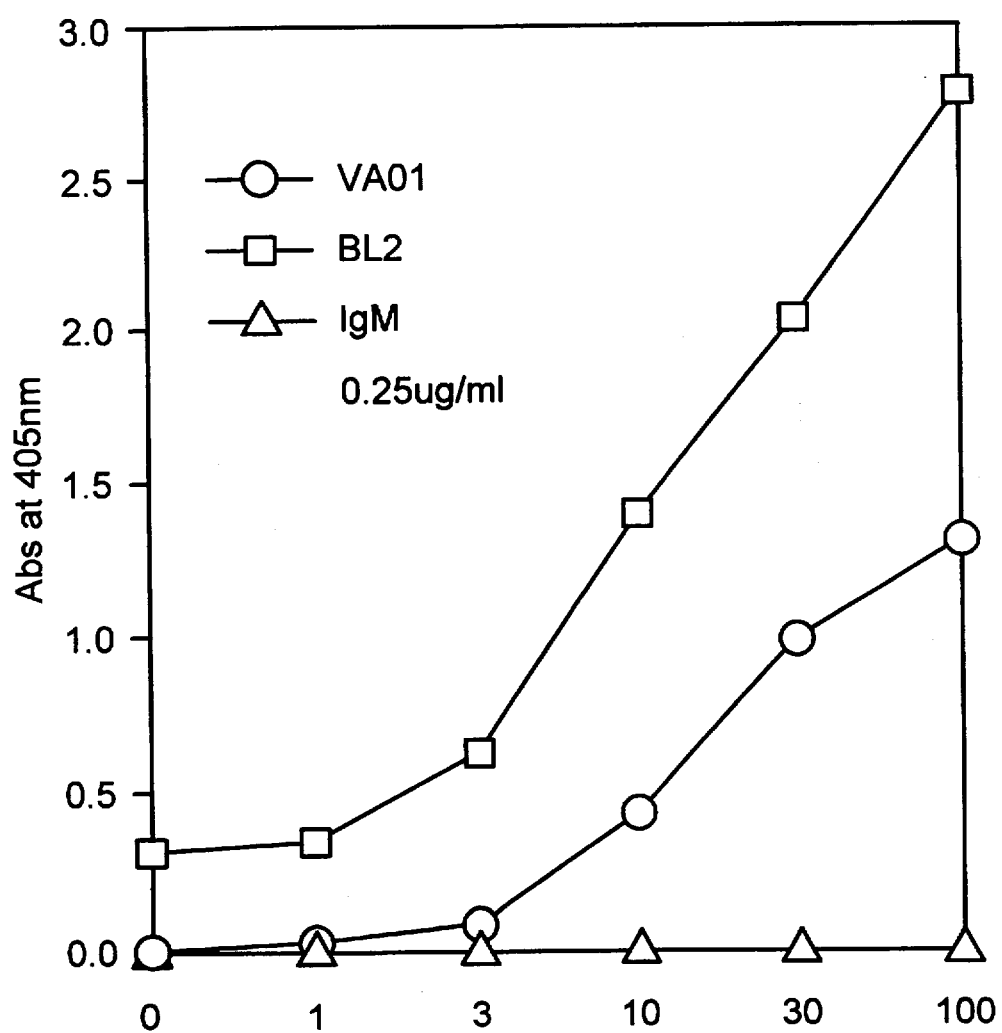
FIG. 2 shows the binding of anti-VEGF human monoclonal antibody to human VEGF antigen in a liquid phase, where BL2 is anti-VEGF human monoclonal antibody purified from hybridoma strain BL2; VA01 is anti-VEGF human monoclonal antibody purified from hybridoma strain VA01; and IgM is human IgM antibody (Rockland). The concentration of each antibody is 0.25 µg/ml.

The results indicated that the antibodies prepared from hybridoma strains VA01 and BL2 react depending on the amount of human VEGF antigen added, as shown in FIG. 2. When the same reaction was carried out using another human IgM antibody (Rockland) of different specificity in place of the VEGF human monoclonal antibody or in the absence of the human monoclonal antibody (control), none of the reaction with human VEGF was observed. This indicated that the anti-VEGF human monoclonal antibody produced by hybridoma strain VA01 and BL2 can recognize human VEGF in liquid phase to bind to it.

EXAMPLE 4
Cross Reactivity

The cross reactivity of the anti-VEGF human monoclonal antibodies purified from hybridoma strains VA01 and BL2 was examined by the DIBA method. The antigens used were recombinant human VEGF (PeproTech), recombinant human basic fibroblast growth factor (Basic FGF; PeproTech), recombinant human platelet derived growth factor-BB (PDGF-BB; PeproTech), recombinant human tumor necrosis factor (TNFα; PeproTech), recombinant human interleukin-8 (IL-8; PeproTech) and recombinant human monocyte chemoattractant protein-1 (MCP-1; PeproTech). Each antigen was dissolved at a concentration of 50 µg/ml in water and the antigen was immobilized in the same manner as in Example 1 (b). The anti-VEGF human monoclonal antibodies purified from hybridoma strains VA01 and BL2 were diluted to 10, 3, 1, 0.3 and 0.1 µg/ml with the blocking solution, and their reactivity toward each of the immobilized antigens at predetermined concentrations was examined in the same manner as in Example 1 (b). The results indicated that the anti-VEGF human monoclonal antibodies of the present invention react strongly with human VEGF but not with other antigens than human VEGF, as shown in Tables 1 and 2.

TABLE 1

Cross reactivity of anti-VEGF human monoclonal antibody VA01

| antigen | reactivity at each concentration of antibody (µg/ml) | | | | | |
|---|---|---|---|---|---|---|
| | 10 | 3 | 1 | 0.3 | 0.1 | 0 |
| VEGF | +++ | +++ | +++ | +++ | +++ | − |
| Basic FGF | − | − | − | − | − | − |
| PDGF-BB | − | − | − | − | − | − |
| TNFα | − | − | − | − | − | − |
| IL-8 | − | − | − | − | − | − |
| MCP-1 | − | − | − | − | − | − |

+++: significantly strong reaction
−: no reaction

TABLE 2

Cross reactivity of anti-VEGF human monoclonal antibody BL2

| antigen | reactivity at each concentration of antibody (µg/ml) | | | | | |
|---|---|---|---|---|---|---|
| | 10 | 3 | 1 | 0.3 | 0.1 | 0 |
| VEGF | +++ | +++ | +++ | +++ | +++ | − |
| Basic FGF | − | − | − | − | − | − |
| PDGF-BB | − | − | − | − | − | − |
| TNFα | − | − | − | − | − | − |
| IL-8 | − | − | − | − | − | − |
| MCP-1 | − | − | − | − | − | − |

+++: significantly strong reaction
−: no reaction

Figure 3:
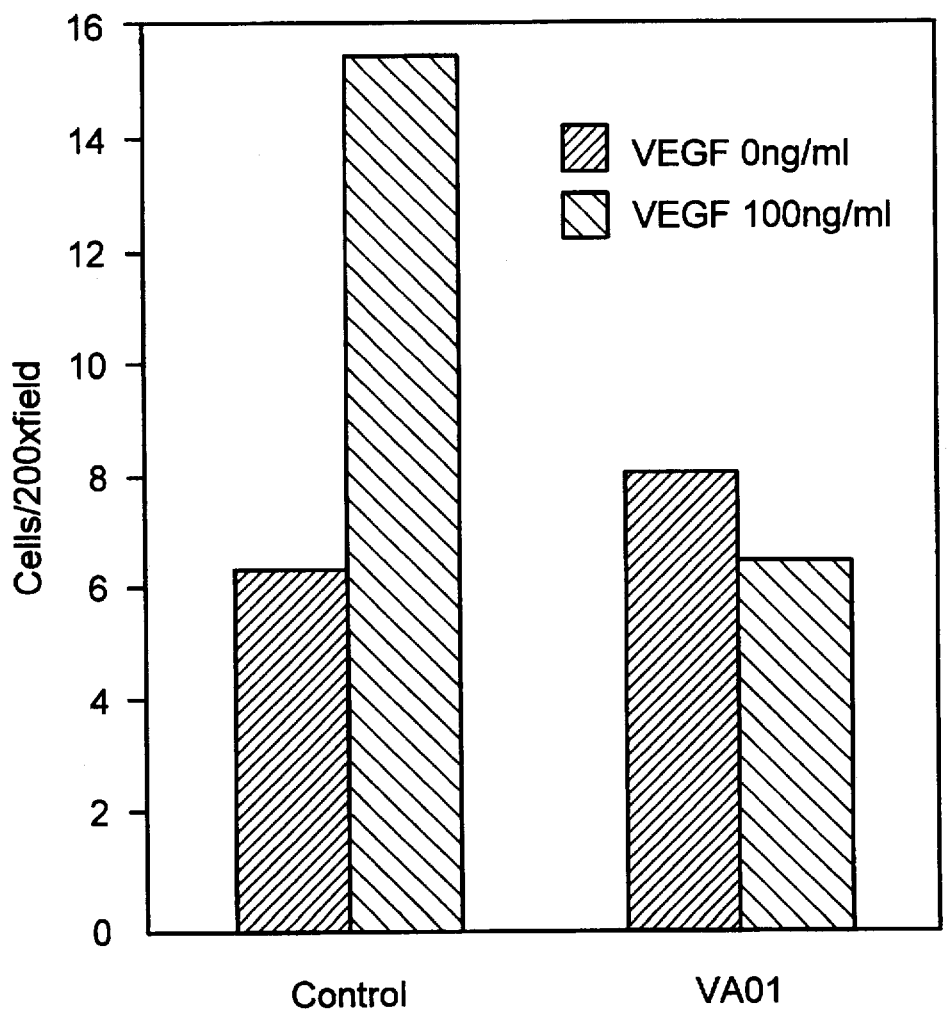
FIG. 3 shows the ability of anti-VEGF human monoclonal antibody to inhibit the migration of vascular endothelial cells, where VA01 is anti-VEGF human monoclonal antibody purified from hybridoma strain VA01.

EXAMPLE 5
Neutralization Test of the Migration Activity of Vascular Endothelial Cells The effect of the human monoclonal antibodies on the wandering activity of vascular endothelial cells induced by human VEGF as one step of vascularization was examined. Human umbilical venous endothelial cells (HUVECs) were suspended in Hanks' solution (Nissui Seiyaku) to a density of $8 \times 10^5$ cells/ml and then 25 µl of the suspension was put to a bottom plate of a 48-wells chemotaxis chamber (Neuroprobe). A membrane filter with a pore size of 5.0 µm (Neuroprobe) and a top plate were attached to the bottom plate, and the assembly was placed upside down for 120 minutes in a $CO_2$ gas incubator at 37° C. so that the HUVECs adhered to the membrane filter. Separately, anti- VEGF human monoclonal antibody purified from hybridoma strain VA01 and human VEGF antigen (PeproTech) were mixed at final concentrations of 34 μg/ml and 100 ng/ml, respectively, and then they were reacted at 37° C. for 30 minutes. Physiological saline (Nissui Seiyaku) was used as a control in place of the anti-VEGF human monoclonal antibody. 50 μl of the reactant was added to the top plate and left for 120 minutes in a $CO_2$ gas incubator at 37° C. The membrane filter was removed and stained with Diff-Quick staining solution (The Green Cross Corporation, Japan) and then the migration cells were observed under a microscope at 200× magnification, and their number was counted. The result indicated that the anti-VEGF human monoclonal antibody purified from hybridoma strain VA01 inhibits the migration of HUVECs by human VEGF antigen, as shown in FIG. 3.

EXAMPLE 6

Neutralization Test of the Proliferation Activity of Vascular Endothelial Cells

Figure 4:
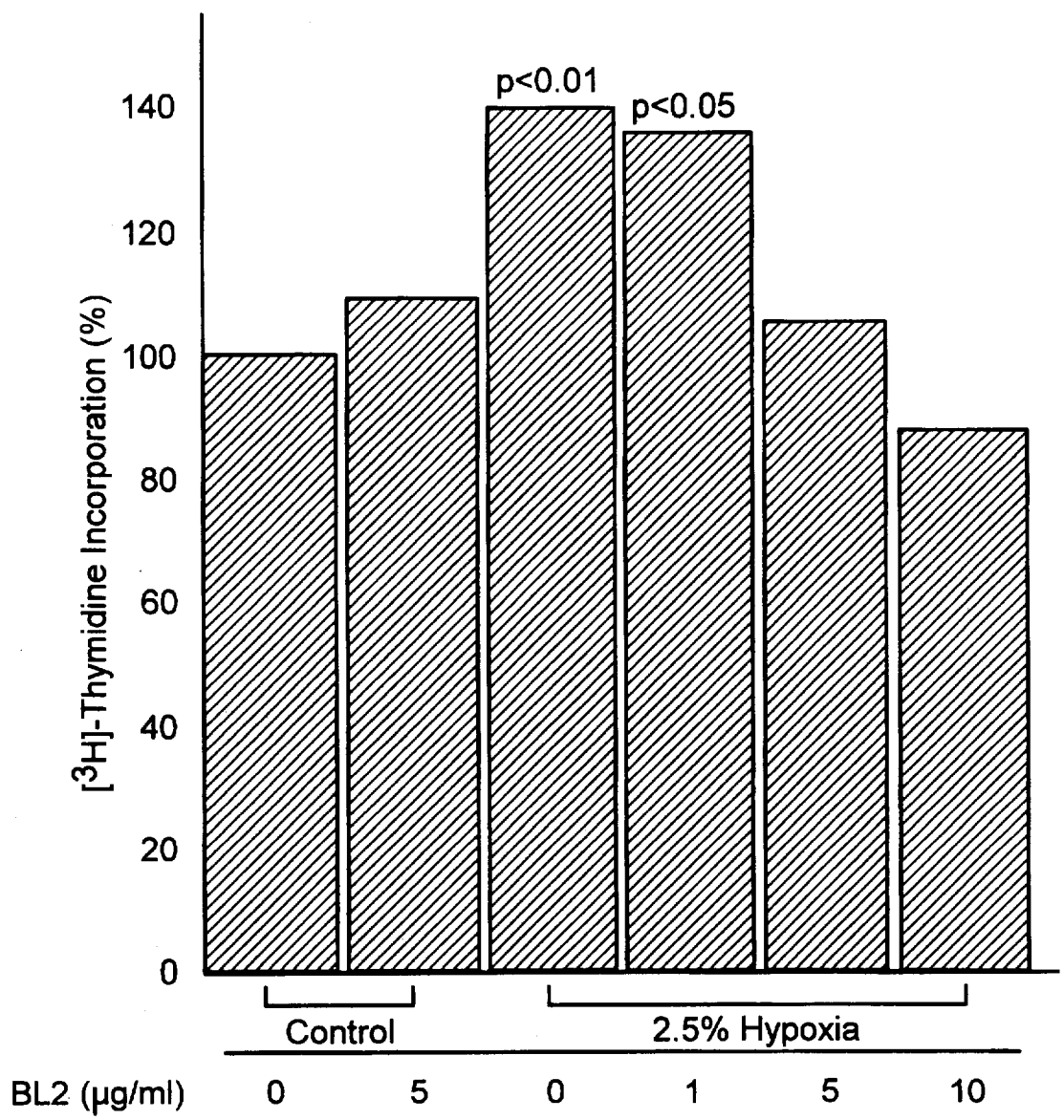
FIG. 4 shows the ability of anti-VEGF human monoclonal antibody to inhibit the proliferation of vascular endothelial cells, where BL2 is anti-VEGF human monoclonal antibody purified from hybridoma strain BL2.

The effect of the anti-VEGF human monoclonal antibody on the proliferation activity of vascular endothelial cells was examined. This proliferation activity, which is induced in a low oxygen atmosphere and considered to trigger tumor vascularization, was determined as follow. Microvascular endothelial cells (Kurabo) derived from human skin was suspended in E-GM MV medium (Kurabo) at $2 \times 10^4$ cells/ml and 500 μl of the suspension was put to a 24-wells plate. The cells were incubated overnight in a $CO_2$ gas incubator at 37° C., and then the medium was replaced by 500 μl fresh RPMI/M199 medium containing 15% (v/v) fetal bovine serum. The anti-VEGF human monoclonal antibody purified from hybridoma strain BL2 was added to the wells in amounts of 0, 1, 5, and 10 μg/ml respectively, then left in a $CO_2$ gas incubator at 37° C. for 30 minutes, and incubated overnight in a low oxygen atmosphere (2.5% $O_2$) or in a conventional atmosphere (control) in the $CO_2$ gas incubator at 37° C. [3H]-thymidine was added to the wells at a final concentration of 1 μCi/ml and they were reacted for 4 hours and gently washed twice with PBS, and then 200 μl of 10% (v/v) cold TCA was added to the cells to fix them. After 20 minutes, the cells were gently washed twice with 5% (v/v) cold TCA and reacted for 20 minutes by adding 200 μl of 1N NaOH. Then, 200 μl of 1 N HCl was added to the cells and the incorporation of [3H]-thymidine into the cells was determined. The result indicated that the anti-VEGF human monoclonal antibody purified from hybridoma strain BL2 inhibits the proliferation of the vascular endothelial cells by autocrine VEGF, as shown in FIG. 4.

What is claimed is:

1. A human monoclonal antibody which specifically binds human vascular endothelial cell growth factor (human VEGF), and inhibits human VEGF promoted vascularization of vascular endothelial cells wherein such human monoclonal antibody is produced by hybridoma BL2, which has been deposited under Accession No. FERM BP-5424 or hybridoma VA01, which has been deposited under Accession No. FERM BP-5607.

2. The human monoclonal antibody of claim 1, which is produced by hybridoma BL2, having Accession No. FERM BP-5424.

3. The human monoclonal antibody of claim 1, which is produced by hybridoma VA01, having Accession No. FERM BP-5607.

4. A composition comprising a human monoclonal antibody according to claim 1.

5. A composition comprising a human monoclonal antibody according to claim 2.

6. A composition containing a monoclonal antibody according to claim 3.

7. Hybridoma BL2, having Accession No. FERM BP-5424.

8. Hybridoma VA01, having Accession No. FERM BP-5607.

* * * * *